United States Patent
Kumano et al.

(10) Patent No.: US 7,202,380 B2
(45) Date of Patent: Apr. 10, 2007

(54) PRODUCTION METHOD OF PYROMELLITIC ACID AND PYROMELLITIC ANHYDRIDE

(75) Inventors: Tatsuyuki Kumano, Okayama (JP); Seiji Adachi, Okayama (JP); Hiroshi Ogawa, Okayama (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 483 days.

(21) Appl. No.: 10/755,394

(22) Filed: Jan. 13, 2004

(65) Prior Publication Data

US 2004/0143135 A1 Jul. 22, 2004

(30) Foreign Application Priority Data

Jan. 16, 2003 (JP) ............................. 2003-008060

(51) Int. Cl.
*C07C 51/235* (2006.01)
(52) U.S. Cl. ..................................... 562/421; 549/239
(58) Field of Classification Search ...................... None
See application file for complete search history.

(56) References Cited

U.S. PATENT DOCUMENTS 4,824,992 A 4/1989 Tanaka et al.

2002/0049339 A1 * 4/2002 Tanaka et al. ............. 549/239

FOREIGN PATENT DOCUMENTS

EP 1052239 11/2000
JP 3-294272 12/1991

OTHER PUBLICATIONS

Communication and European Search Report mailed Jul. 5, 2004, for No. EP 04 00 0042.
Chinese Official Action, for application No. 200410002257.7, dated Oct. 13, 2006.

* cited by examiner

*Primary Examiner*—Brian Davis
(74) *Attorney, Agent, or Firm*—Antonelli, Terry, Stout & Kraus, LLP.

(57) ABSTRACT

In a method of producing pyromellitic acid by liquid-phase oxidizing 2,4,5-trimethylbenzaldehyde in a water solvent with molecular oxygen, a recrystallization mother liquor separated in a recrystallization step is recycled to the oxidation step after a part of the water solvent is removed. With this method, the loss of pyromellitic acid and the oxidation catalyst can be minimized and the burden of discharging the waste water is reduced without lowering the efficiency of the liquid-phase oxidation reaction.

11 Claims, 1 Drawing Sheet

PRODUCTION METHOD OF PYROMELLITIC ACID AND PYROMELLITIC ANHYDRIDE

BACKGROUND OF THE INVENTION

1. Field of the Invention

The present invention relates to the production of pyromellitic acid and pyromellitic anhydride. These compounds are usable in a wide variety of applications, for example, the production of various resins such as polyimide for electronic materials, specialty plasticizers and epoxy hardeners.

2. Description of the Prior Art

Japanese Patent Application Laid-Open No. 56-26839 discloses a method of producing pyromellitic acid by a liquid-phase oxidation of 2,4,5-trimethylbenzaldehyde (hereinafter referred to as "TBAL") by air in the presence of a catalyst comprising a bromine compound and a heavy metal. Japanese Patent Application Laid-Open No. 58-121244 proposes to reduce catalyst costs by separating the aqueous oxidation solution into crude crystals of pyromellitic acid and a mother liquor and recycling the separated mother liquor into the oxidation reactor. The crude crystals of pyromellitic acid obtained by the oxidation in a water solvent can be purified by the recrystallization from water. However, since the recrystallization mother liquor dissolves a part of the produced pyromellitic acid and the heavy metal salt thereof, the recrystallization yield becomes lower and the catalyst costs becomes larger. The discharge of all the liquids separated from the production steps as the process waste water imposes a very large burden on the production method and economy. If the liquid as separated is reused as a part of the solvent for the oxidation, the activity of the oxidation catalyst is reduced because of excessive dilution to reduce the oxidation efficiency.

SUMMARY OF THE INVENTION

An object of the present invention is to provide a cost-reduced and environmentally friend method of producing pyromellitic acid and pyromellitic anhydride in which the loss of pyromellitic acid and the oxidation catalyst is minimized and the burden of discharging the waste water is reduced.

As a result of extensive study in view of solving the above problems, the inventors have found that the loss of pyromellitic acid and the oxidation catalyst is minimized and the amount of process waste water is reduced without reducing the activity of the oxidation catalyst and deteriorating the quality of the purified pyromellitic acid crystal, by separating a mother liquor (recrystallization mother liquor) from the step for recrystallizing pyromellitic acid and then recycling the separated mother liquor, after removing a part of the water solvent, to the oxidation step and, if necessary, also to the recrystallization step as a part of the solvent. The inventors have further found that, by utilizing the reaction heat generated in the oxidation of TBAL, an additional external heating can be omitted for the removal of a part of the water solvent from the separated recrystallization mother liquor, thereby producing pyromellitic acid and pyromellitic anhydride advantageously in view of energy saving. The present invention has been accomplished on the basis of these findings.

Thus, the present invention provides a method of producing pyromellitic acid, which comprises: a step of liquid-phase oxidizing 2,4,5-trimethylbenzaldehyde (TBAL) by molecular oxygen in water solvent; a step of separating the reaction liquid from the liquid-phase oxidation step into crude crystals of pyromellitic acid and a mother liquor; a step of recrystallizing the crude crystals of pyromellitic acid from water solvent; a step of separating the recrystallization mixture into a recrystallized pyromellitic acid and a recrystallization mother liquor; a step of removing a part of the water solvent from the separated recrystallization mother liquor, thereby obtaining a condensed recrystallization mother liquor; and a step of recycling the condensed recrystallization mother liquor at least to the liquid-phase oxidation step.

The present invention further provides a method of producing pyromellitic anhydride, which comprises a step of converting pyromellitic acid produced by the above method into pyromellitic anhydride.

DETAILED DESCRIPTION OF THE INVENTION

Figure 1:
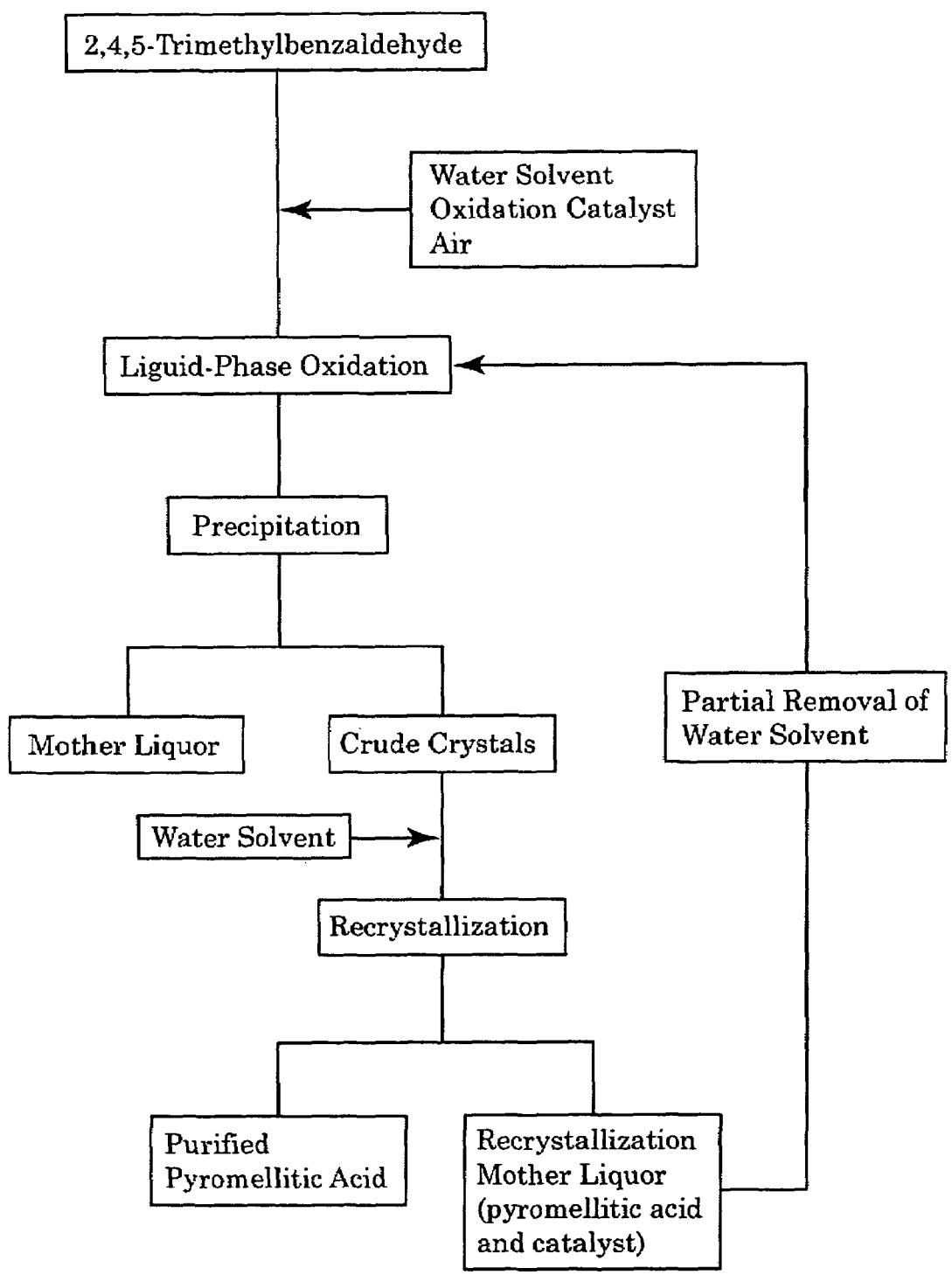
FIG. 1 is a flow chart showing one example of a manner for recycling a recrystallization mother liquor.

The method of producing pyromellitic acid of the present invention includes the step of liquid-phase oxidizing TBAL by molecular oxygen in water solvent; the step of precipitating crude crystals of pyromellitic acid from the reaction liquid after the liquid-phase oxidation; the step of separating the reaction liquid into crude crystals of pyromellitic acid and a mother liquor; the step of recrystallizing the crude crystals of pyromellitic acid from water solvent; the step of separating the recrystallization mixture into a recrystallized pyromellitic acid and a recrystallization mother liquor; and the step of recycling the separated recrystallization mother liquor at least to the oxidation step after removing a part of the water solvent from the separated recrystallization mother liquor. The method of producing pyromellitic anhydride of the present invention further includes the step of converting the recrystallized pyromellitic acid obtained by the method as mentioned above into pyromellitic anhydride.

As the oxidation catalyst, a bromine compound and a heavy metal compound are combinedly used. The bromine compound is not particularly limited as far as it is capable of generating bromide ion in the liquid-phase oxidation system, and includes, for example, hydrogen bromide, ammonium bromide, sodium bromide and organic bromine compounds such as alkyl bromides. As the heavy metal compounds, those capable of generating heavy metal ion in the liquid-phase oxidation system are used. Examples thereof include compounds, for example, halides, organic acid salts and carbonates, of manganese, cerium, cobalt, nickel, zirconium and iron, with acetate or bromide of manganese or cerium being preferred. The addition amount of the bromine compound is 0.5 to 12% by weight, preferably 0.5 to 6% by weight in terms of bromide ion based on the water solvent. The heavy metal compound is preferably added in an amount that generates in the liquid-phase oxidation system an equivalent amount of heavy metal ion to bromide ion. More preferably, the addition amount of the heavy metal compound is 0.1 to 1.5% by weight in terms of heavy metal ion based on the water solvent.

The amount of water as the solvent is not specifically limited, and preferably one part by weight or more, more preferably 4 to 12 parts by weight based on one part by weight of TBAL. Any oxidizing agent may be used as far as it contains molecular oxygen. Examples thereof include oxygen gas and air, with air being preferred because of its economic advantage. The reaction temperature is 180 to 280° C., preferably 200 to 260° C. The reaction pressure is not specifically limited as far as the liquid-phase oxidation system is maintained in the liquid phase, and generally 1.5 to 6 MPa. The liquid-phase oxidation reaction may be conducted in either of batch wise, semi-batch wise or continuous manner, with the continuous manner being preferred.

After the liquid-phase oxidation, the reaction liquid is cooled to 20 to 60° C. to precipitate pyromellitic acid, and then separated into crude crystals of pyromellitic acid and a mother liquor by solid-liquid separation. The mother liquor remaining on the crude crystals is removed by rinsing or reslurrying. The separated mother liquor may be reused, if necessary, together with the used rinsing liquid by recycling to the liquid-phase oxidation step and/or the precipitation step. Water is particularly preferred as the rinsing liquid. Then, the crude crystals of pyromellitic acid is redissolved in water and purified by recrystallization. The amount of water as the recrystallization solvent is not specifically limited, and preferably 1 to 10 parts by weight based on one part by weight of the crude crystals of pyromellitic acid. The recrystallization temperature and pressure are not specifically limited as far as the crude crystals are dissolved, and preferably 50 to 150° C. and 0.01 to 0.5 MPa. After redissolution, the liquid is cooled to 20 to 60° C. and separated into the purified crystals of pyromellitic acid and the recrystallization mother liquor by solid-liquid separation. The mother liquor remaining on the purified crystals is removed by rinsing or reslurrying. Water is particularly preferred as the rinsing liquid.

The separated recrystallization mother liquor together with, if necessary, the used rinsing liquid is recycled at least to the liquid-phase oxidation step and optionally to the recrystallization step. Since the recrystallization mother liquor contains the oxidation catalyst and pyromellitic acid, the loss of the catalyst and pyromellitic acid is minimized by recycling the recrystallization mother liquor to the liquid-phase oxidation step. However, if the recrystallization mother liquor as separated is recycled to the liquid-phase oxidation step, the efficiency of the liquid-phase oxidation is reduced because the catalyst is excessively diluted to lower its activity. Therefore, the recrystallization mother liquor is recycled to the liquid-phase oxidation step after a part of the water solvent is removed. The amount of the water solvent to removed is regulated so that the concentration of the catalyst, i.e., the bromide ion concentration and the heavy metal ion concentration, comes within the range mentioned above. The partial removal of the water solvent is preferably conducted by evaporation utilizing the heat generated in the liquid-phase oxidation. By utilizing the reaction heat, the additional external heating is made needless to save the energy, thereby making the process industrially advantageous. The removed water can be reused in other steps or drained as general waste water.

The purified crystals of pyromellitic acid is converted to pyromellitic anhydride in the dehydration step by a heat dehydration method or an acetic anhydride method. The heat dehydration is conducted by known method, for example, by heating the purified crystals of pyromellitic acid at 190 to 270° C. under 0.02 to 2 MPa for 0.1 to 24 h. The acetic anhydride method is conducted, for example, by heating a mixture of one part by weight of the purified crystals of pyromellitic acid and 1 to 20 parts by weight of acetic anhydride at reflux temperature under atmospheric pressure for 0.5 to 24 h.

In the liquid-phase oxidation of TBAL, water is by-produced. Therefore, the liquid-phase oxidation and the recycling of the recrystallization mother liquor produce the surplus water in the process. The surplus water is recovered as a pure water by evaporation and reused in other steps, for example, as a rinsing liquid. The surplus water can be recovered by evaporating the aqueous solutions from each step of the process (reaction solution, precipitation mother liquor, recrystallization mother liquor, etc.) under heating with a heat exchanger, etc. However, it is industrially preferred to recover a part of the refluxed water in the liquid-phase oxidation or recover the water vaporized by the pressure difference between the oxidation apparatus and the recrystallization apparatus. With such a manner, the surplus water is recovered as a pure water at low costs.

Since the solvents used in the production method of the present invention are all water, the surplus water can be efficiently recovered as mentioned above. A production method using a solvent other than water, for example, a water-containing acetic acid, requires additional apparatus, operation and costs because an additional separation step by distillation is needed to separate water. Since water and pyromellitic acid inhibit the oxidation of TBAL in a method using a solvent other than water, it is practically difficult in such a method to recycle the recrystallization mother liquor to the oxidation step. Making the best use of the advantage of the production method using only the water solvent, the present invention provides an efficient and environmentally friend production method of pyromellitic acid and pyromellitic anhydride.

The present invention will be explained in more detail by reference to the following example which should not be construed to limit the scope of the present invention thereto.

EXAMPLE 1

According to the production process shown in FIG. 1, pyromellitic acid was produced as described below.

After the liquid-phase oxidation of TBAL and the subsequent precipitation, wet crude crystals of pyromellitic acid (58% by weight purity) were obtained. The wet crude crystals and water were fed to the recrystallization step at respective feeding speeds of 1.0 part by weight and 1.2 parts by weight to redissolve the crude crystals to water at 120° C. under 0.2 MPa. Then, the solution was cooled to 40° C. for recrystallization. The resultant slurry was solid-liquid separated to obtain purified crystals of pyromellitic acid, which were then rinsed with water of 0.80 part by weight/h. As a result, a recrystallization mother liquor containing 4.6% by weight of pyromellitic acid and 0.006% by weight of manganese was obtained in an amount of 2.1 parts by weight per one hour. After condensing, the recrystallization mother liquor was continuously recycled to the liquid-phase oxidation step as a part (44% by weight) of the water solvent. As a result of the continued production of pyromellitic acid, 0.49 part by weight of pyromellitic acid was obtained. The surplus water produced during the recycling was recovered from the system in an amount of 2.0 parts by weight per one hour as the refluxed water and flash-vaporized water respectively in the liquid-phase oxidation step and the precipitation step. The purity of the recovered water was 99.8% by weight or more, and the loss of pyromellitic acid and the catalyst was extremely small.

Comparative Example 1

The procedure of Example 1 was repeated except for omitting the recycling of the separated recrystallization mother liquor. The yield of pyromellitic acid was lower than that of Example 1 by 0.04 part by weight per one hour. In addition, the waste water contained about 4.6% by weight of pyromellitic acid and about 0.006% by weight of manganese, thereby failing to prevent the loss of pyromellitic acid and the oxidation catalyst.

As evidenced by the above example, the present invention provides an efficient and environmentally friend method of producing pyromellitic acid and pyromellitic anhydride with a minimized loss of pyromellitic acid and the oxidation catalyst and a reduced burden of discharging the waste water.

What is claimed is:

1. A method of producing pyromellitic acid, which comprises:
    a step of liquid-phase oxidizing 2,4,5-trimethylbenzaldehyde by molecular oxygen in water solvent;
    a step of separating the reaction liquid from the liquid-phase oxidation step into crude crystals of pyromellitic acid and a mother liquor;
    a step of recrystallizing the crude crystals of pyromellitic acid from water solvent to obtain a recrystallization mixture;
    a step of separating the recrystallization mixture into a recrystallized pyromellitic acid and a recrystallization mother liquor;
    a step of removing a part of the water solvent from the separated recrystallization mother liquor, thereby obtaining a condensed recrystallization mother liquor; and
    a step of recycling the condensed recrystallization mother liquor at least to the liquid-phase oxidation step,
    wherein a surplus water produced by at least one of the liquid-phase oxidation and the recycling of the recrystallization mother liquor is recovered by evaporation.

2. The method according to claim 1, wherein the liquid-phase oxidation step is conducted at 180 to 280° C. under a pressure of 1.5 to 6 MPa in the presence of a catalyst comprising a bromine compound and a heavy metal compound.

3. The method according to claim 2, wherein the bromine compound is added in an amount of 0.5 to 12% by weight in terms of bromide ion based on the water solvent, and the heavy metal compound is added in an amount that generates an equivalent amount of heavy metal ion to bromide ion.

4. The method according to claim 1, wherein the step of removing apart of the water solvent from the separated recrystallization mother liquor is conducted by utilizing a heat generated in the liquid-phase oxidation step.

5. A method of producing pyromellitic anhydride comprising a step of converting the pyromellitic acid produced by the method as defined in claim 1 to pyromellitic anhydride.

6. The method according to claim 5, wherein the step of converting the pyromellitic acid to pyromellitic anhydride is conducted by heating the pyromellitic acid at 190 to 270° C. under a pressure of 0.02 to 2 MPa for 0.1 to 24 h.

7. The method according to claim 1, wherein the surplus water is recovered from a part of refluxed water in the liquid-phase oxidation step and/or from water vaporized by a pressure difference between oxidation apparatus and recrystallization apparatus.

8. The method according to claim 1, wherein amount of water as solvent in the liquid-phase oxidation is at least one part by weight based on one part by weight of the 2,4,5-trimethylbenzaldehyde.

9. The method according to claim 1, wherein the evaporation to recover the surplus water is performed using heat generated by the liquid-phase oxidation.

10. The method according to claim 1, wherein the recovered water is reused in the method.

11. The method according to claim 3, wherein the amount of water removed in the step of removing a part of the water solvent from the separated recrystallization mother liquor is such that amounts of bromine compound and of heavy metal compound are maintained as said amount of bromine compound and said amount of heavy metal compound.

* * * * *